(12) United States Patent
Hubach et al.

(10) Patent No.: US 6,485,520 B1
(45) Date of Patent: Nov. 26, 2002

(54) WRIST PROSTHESIS

(75) Inventors: Peter C. G. Hubach, Twisk (NL); Bernd Schafer, Goppingen (DE); Thilo Trauwein, Stuttgart (DE)

(73) Assignee: Schafer micomed GmbH, Goppingen (DE)

( * ) Notice: Subject to any disclaimer, the term of this patent is extended or adjusted under 35 U.S.C. 154(b) by 0 days.

(21) Appl. No.: 09/347,924

(22) Filed: Jul. 6, 1999

(51) Int. Cl.[7] .................................................. A61F 2/42
(52) U.S. Cl. .................................................. 623/21.13
(58) Field of Search ........................... 623/21.11, 21.12, 623/57, 61, 62, 18.11, 21.13, 21.14

(56) References Cited

U.S. PATENT DOCUMENTS

| | | | | |
|---|---|---|---|---|
| 5,766,258 A | * | 6/1998 | Simmen | 623/21.11 |
| 5,782,926 A | * | 7/1998 | Lamprecht | 623/21.11 |
| 6,059,832 A | * | 5/2000 | Menon | 623/21.11 |
| 6,168,630 B1 | * | 1/2001 | Keller et al. | 623/21.11 |

* cited by examiner

*Primary Examiner*—David H. Willse
*Assistant Examiner*—Suzette J. Jackson
(74) *Attorney, Agent, or Firm*—Jones, Tullar & Cooper, P.C.

(57) ABSTRACT

A wrist prosthesis has distal and proximal sections, which are connected with one another by a curved bearing.

25 Claims, 4 Drawing Sheets

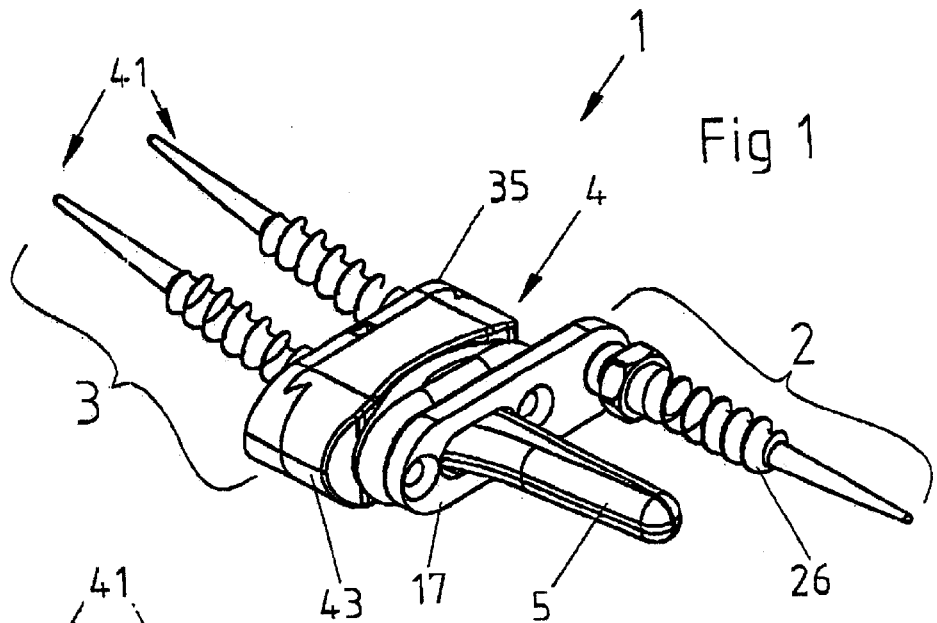
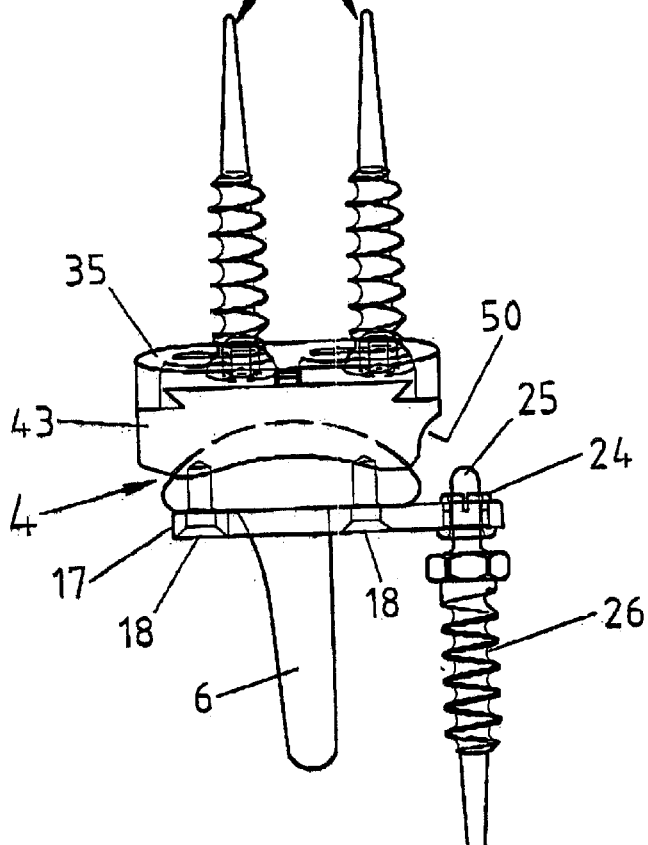
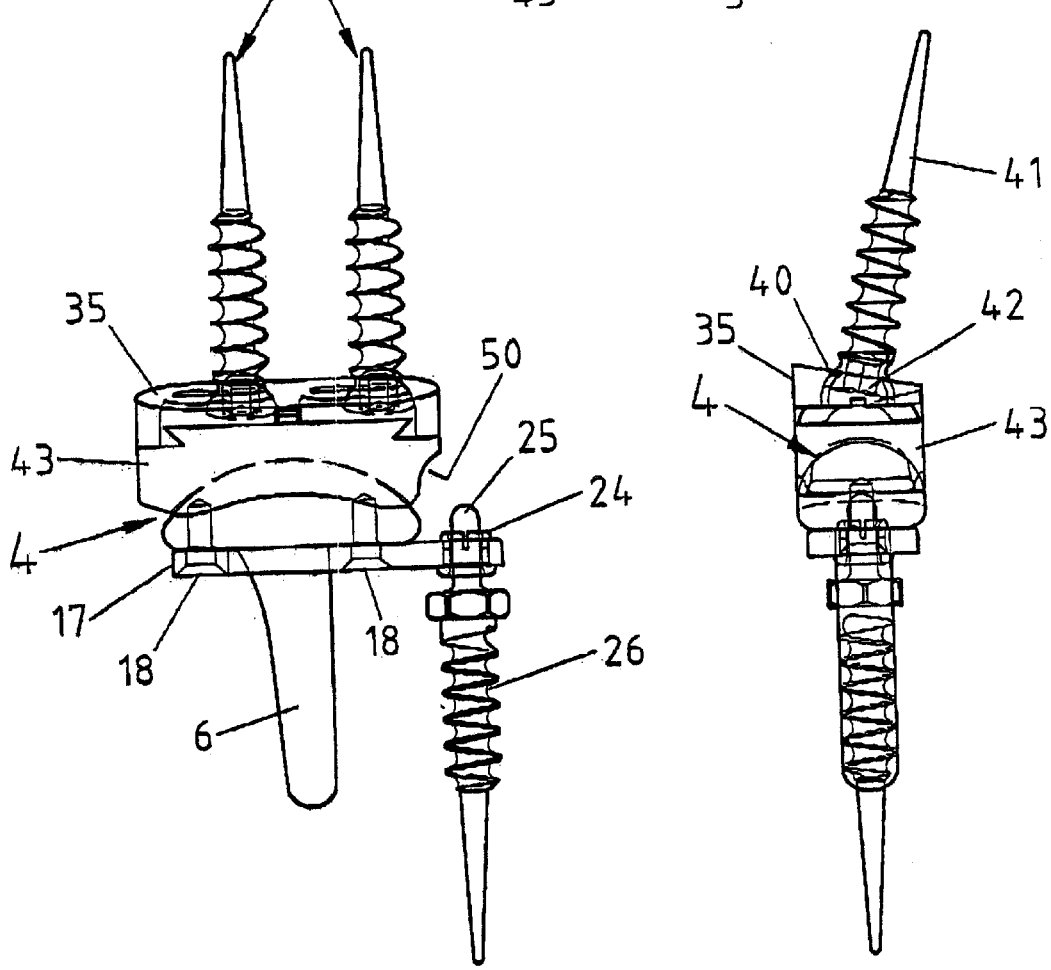

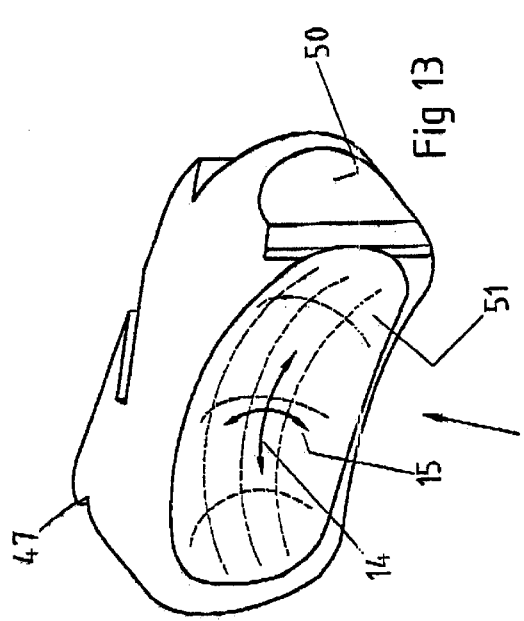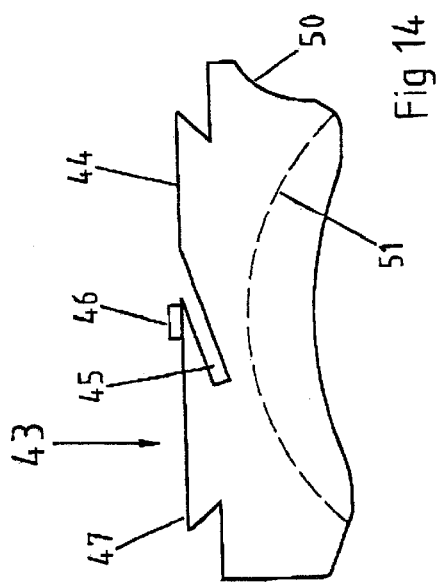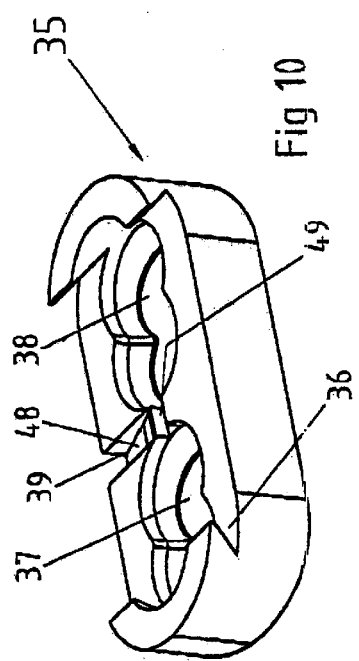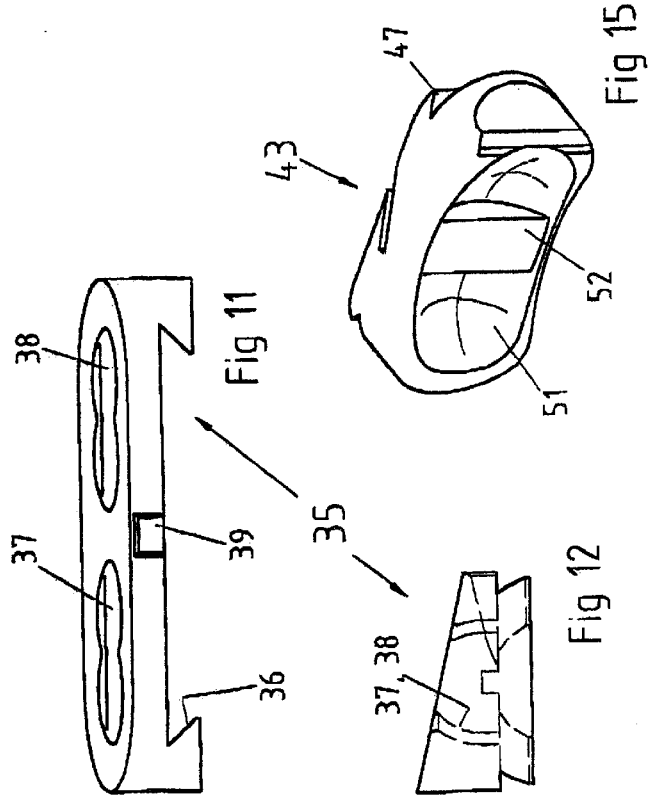

WRIST PROSTHESIS

FIELD OF THE INVENTION

BACKGROUND OF THE INVENTION

The invention relates to a wrist prosthesis having a first, proximal section and a second, distal section. The proximal section connects with the distal end of the radius bone and the distal section with at least one, especially with two, metacarpal bones.

U.S. Pat. No. 5,458,646 shows a wrist prosthesis in which a first, proximal section is connected rigidly with the distal end of the radius and the distal end of the ulna. A second, distal section of the wrist prosthesis is connected with the carpal bones. This second, distal section of the wrist prosthesis has a rounded, proximal end, which abuts on a straight surface of the proximal section. Such a wrist prosthesis has a number of disadvantages. For one, it connects the radius rigidly with the ulna and this limits movement of the wrist in the pronation-supination direction. Additionally, the connection of the distal section of the wrist prosthesis with the carpal bones is inadequate. Finally, such a wrist prosthesis is only usable in cases where osteoporosis has not yet progressed too far, so that it is only conditionally usable or installable.

SUMMARY OF THE INVENTION

An object of the present invention is, therefore, to provide a wrist prosthesis that has a wider range of applicability.

This object is achieved with a wrist prosthesis having a first, proximal section and a second, distal section, wherein the proximal section is connected with the distal end of the radius and the distal section is connected with at least one, especially with two, metacarpal bones, and each of the sections contains one part of a curved bearing.

The wrist prosthesis of the invention can be used advantageously in the case of rheumatoid arthritis. It has the essential advantage that the proximal section is connected rigidly only with the radius. A single anchor serves for this purpose. The anchor is cemented relatively far into the radius. Moreover, the second, distal section of the prosthesis is connected with at least one, especially with two, metacarpal bones, this providing significantly better stability and anchoring. For this purpose, screws are screwed into the metacarpal bones. The screws have a relatively long, thread-free screw tip, which is rounded on the front end. Using this relatively long screw, a secure connecting of the distal section with these bones is assured. Finally, each section exhibits one part of a curved bearing, to assure an optimal support both in the axial direction as well as in all transverse directions.

The anchor preferably has an asymmetric shape and an anchor head extending above the radius bone. This anchor head forms one part of the curved bearing.

In a preferred embodiment, the distal section has a carpal plate, which seats the connecting elements, especially bone screws, which connect to the bones of the hand. The carpal plate has seats for the heads of the screws. Connecting the screws using a carpal plate has the advantage that the distal section of the wrist prosthesis has a relatively stable construction, so that the metacarpal bones experience an optimal support. A stiff and secure connection of the distal section with the hand is achieved. In this way, a loosening is made highly unlikely.

For fitting the wrist prosthesis to different wrist sizes, the seats are expanded essentially lengthwise and in each case have at least two seating positions for the screw heads. These seating positions allow the positions of the screws to be matched to the positions of the metacarpal bones, without necessitating provision of differently configured carpal plates. The carpal plate is thus universally installable.

In a preferred embodiment, the seats for the screws have the form of a figure 8. This makes it possible to have different positions for the screw heads and the separation of the screws from one another becomes adjustable.

In a further, preferred development of the present invention, it is provided that the axes of the seats are inclined in the plane of inclination of the wrist by an angle of 5-degrees to 15-degrees, especially 12-degrees, relative to the axis of the proximal section. The wrist is thus inclined by an angle in the range of 5-degrees to 15-degrees, with this inclined position representing the basic position.

Advantageously, the carpal plate is connected with the proximal section through a bearing element. This bearing element contains the other part of the curved bearing and its size can be fitted to that of the wrist. The different bearing elements thus permit a relatively accurate matching of the wrist prosthesis to the size of the wrist. The bearing element is connected with the carpal plate, for example, using a screw connection, or the bearing element has a dovetail connection, by which it is connected with the carpal plate. The dovetail connection can be provided with a snap-lock connection, so that the coupling of the bearing element to the carpal plate is quick and, above all, accomplished without tools.

In a preferred embodiment of the invention, present the bearing element is provided with a lug, which extends into a groove on the anchor head, or vice versa. This stabilizes the bearing in the pronation-supination direction, while inclination of the bearing remains unimpeded.

A further development provides that the anchor head is shaped on its pin side for reception of an ulna-radius connecting means, especially an ulna plate. If necessary, the anchor can be equipped with this ulna plate. A connection of the radius with the ulna can be produced using this ulna plate. To accomplish this connection, the ulna plate extends laterally beyond the anchor head of the anchor and has a seat for an ulna screw, which is screwed into the end of the ulna.

An insert is provided in the seat for the ulna screw, in order that the ulna screw can have a movable connection with the ulna plate. In this way, it is assured that, despite the connection of the ulna and radius, relative movement between these bones is still possible, as was the case originally. Thus, the wrist is significantly more flexible in the pronation-supination direction.

The ulna screw is journaled in the insert such that it can swivel and/or undergo axial displacement. This movable journaling allows, additionally, a relatively unimpeded rotation of the wrist, but, despite the relatively large freedom of the ulna, it is supported afterwards as before.

Wear resistance in the bearings is achieved by making the bearing element and/or the insert from plastics material, especially polyethylene (PE). The other components can be of steel, and especially titanium, the surface of which is provided with a coating which serves as a substrate promoting bone growth. An example of such a known coating is referred to as HA-coating, where HA stands for hydroxy apatite.

A problem-free movement of the wrist is made possible by providing the curved bearing with a circular arc curvature in both the pronation-supination direction and in the inclination direction.

A high installability for the wrist of the present invention is achieved by forming the proximal and/or the distal section of the wrist prosthesis from modularly combinable components, which, if necessary, can have different sizes. The separate modules can be assembled on site, i.e. during the operation. These can e.g. be differently thick and/or differently long bone screws, differently sized carpal plates, differently sized bearing elements, differently sized ulna plates, and differently thick and long anchors, as well as differently sized ulna screws.

Other advantages, features and details will be perceived from the appended claims as well as from the following description, in which especially preferred embodiments are explained in detail with reference to the drawings. Features shown in the drawings, stated in the claims, or related in the description can be inventive, whether taken singly or in various combinations.

BRIEF DESCRIPTION OF THE DRAWINGS

FIG. 1 is a perspective view of a preferred embodiment of the wrist prosthesis of the PRESENT invention;

FIG. 2 is a view on the narrow side of the wrist prosthesis of FIG. 1;

FIG. 3 is a view on the broad side of the wrist prosthesis of FIG. 1;

FIG. 10 is a perspective view of the carpal plate;

FIG. 11 is a view on a broad side of the carpal plate of FIG. 10;

FIG. 12 is a view on a narrow side of the carpal plate of FIG. 10;

FIG. 13 is a perspective view of the bearing element connectable with the carpal plate of FIG. 10;

FIG. 14 is a side view of the bearing element; and

FIG. 15 is a side view of a further embodiment of the bearing element.

DESCRIPTION OF THE PREFERRED EMBODIMENTS

Figure 4:
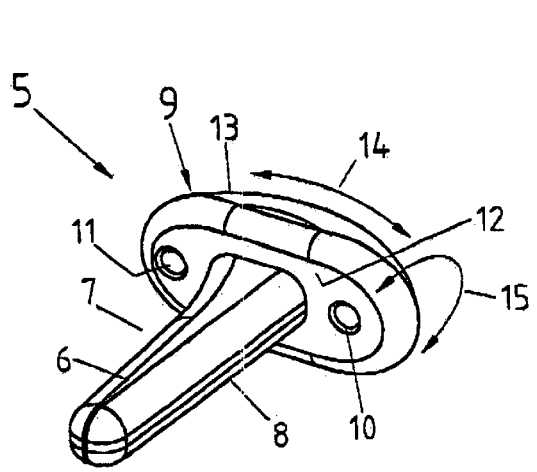
FIG. 4 is a perspective view of the anchor of the wrist prosthesis.

FIG. 1 shows an especially preferred embodiment of an assembled wrist prosthesis 1 of the present invention. This wrist prosthesis 1 has a first, proximal section 2 and a second, distal section 3. The two sections 2 and 3 are connected flexibly together by a curved bearing 4, which can be better seen in FIGS. 2 and 3.

The proximal section 2 has an anchor 5, which is shown in detail in FIG. 4. Anchor 5 has an asymmetrically shaped pin 6, whose pronation side 7 is curved and whose supination side 8 is straight. Pin 6 has a rounded tip and broadens in the direction of its anchor head 9. Anchor head 9 has two threaded bores 10 and 11 on its underside, these bores being arranged on both sides of pin 6. Threaded bores 10 and 11, as well as pin 6, are located in a recess 12 on the underside of anchor head 9. Recess 12 has the purpose of providing room for excess cement during the cementing of anchor 5 into the radius of a forearm. The side of anchor head 9 lying opposite to pin 6 forms one part 13 of the curved bearing 4. Bearing part 13 has a convex or circular arc shape both in the longitudinal direction (arrow 14) and in the transverse direction (arrow 15). The arc radius is greater in the longitudinal direction than in the transverse direction. These two circular arc curvatures make pivoting possible in both the longitudinal direction and in the transverse direction (i.e. both in the pronation-supination direction and in the inclination direction), while a twisting of the curved bearing 4 is inherently prevented.

Figure 5:
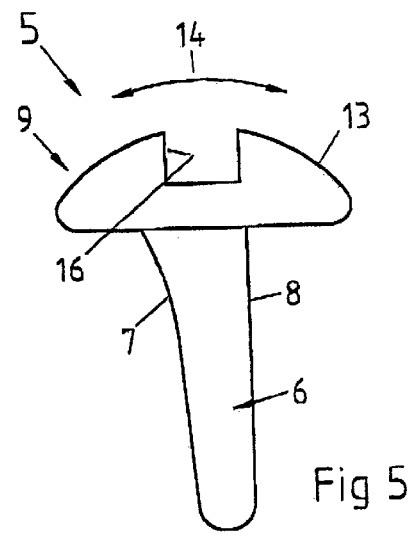
FIG. 5 is a side view of a second embodiment of the anchor.

FIG. 5 shows a second embodiment of an anchor 5, the anchor head 9 of which is provided with a groove 16 running in the transverse direction of the arrow 15. The function of groove 16 will be explained below, in the discussion of FIG. 15.

Figure 6:
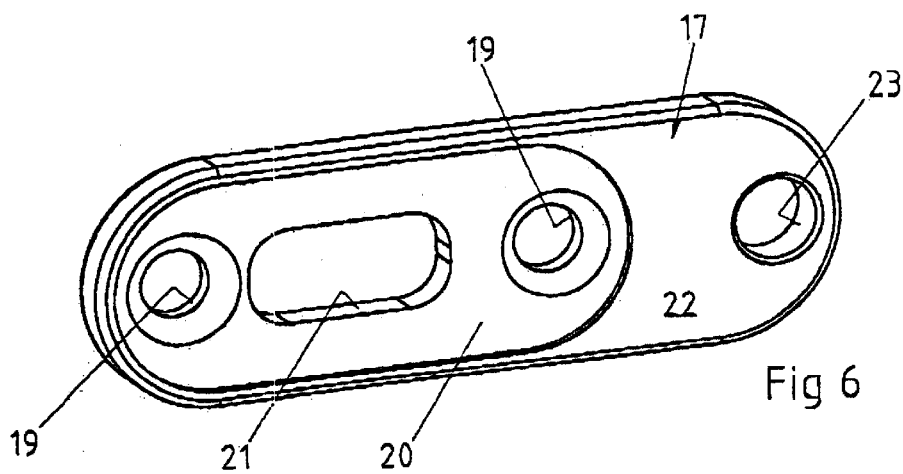
FIG. 6 is a view on the underside of the ulna plate.

FIG. 6 shows an ulna plate 17, which can also be seen in FIGS. 1 to 3. Ulna plate 17 is connected by screws 18 with the underside of anchor head 9. The screw heads are seated in countersunk holes 19 on the ulna plate, and the screws are screwed into the threaded bores 10 and 11. Ulna plate 17 also has a recess 29 serving to provide room for excess cement. Pin 6 is guided through plate 17 through the elongated openings 21.

Ulna plate 17 extends laterally 7 beyond the anchor head 9 with a section 22, which as shown (FIGS. 1 to 3 and 6), lies in the same plane of the ulna plate. In both embodiments (not shown), section 22 can be offset downwards, i.e. in the direction of pin 6. Opening 21 and section 22 lie in two mutually separated, parallel plans. It is, however, conceivable to have section 22 lie at an angle to the plane of opening 21.

Figures 7, 8:
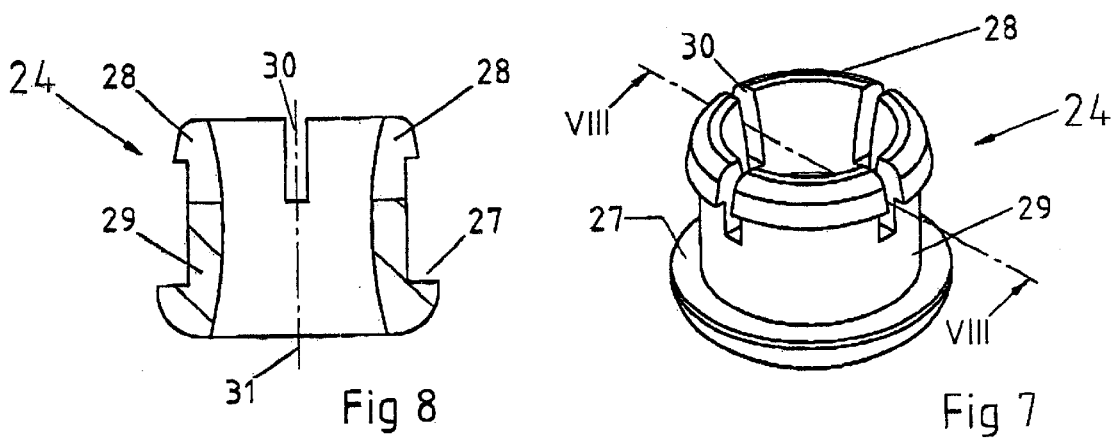
FIG. 7 is a perspective view of an insert that snaps into the ulna plate.
FIG. 8 is a longitudinal section VIII-VIII through the insert according to FIG. 7.
Figure 9:
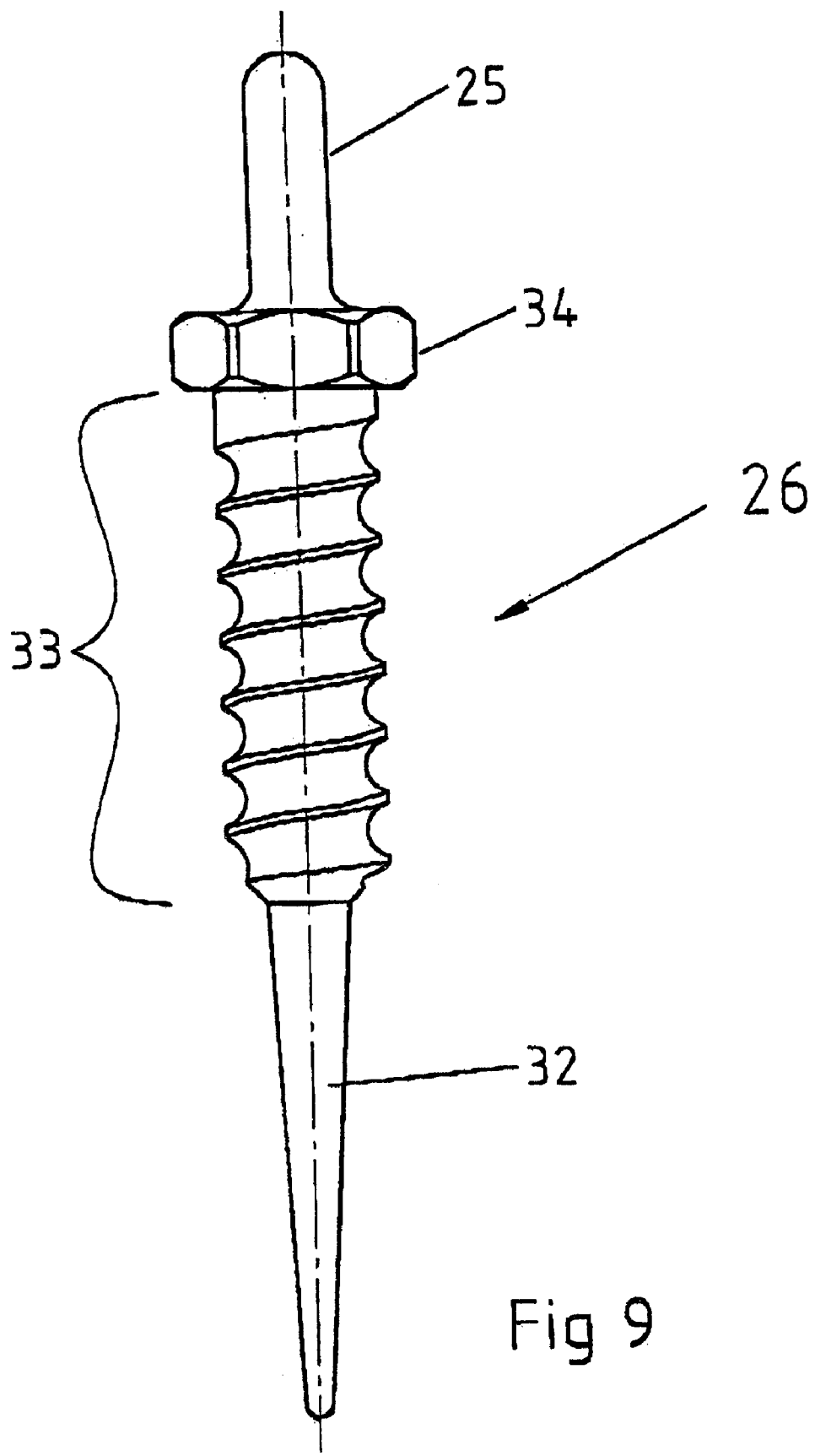
FIG. 9 is a side view of the ulna screw.

Section 22 has an opening 23, in which an insert 24 snaps in place. This insert 24 is shown in FIGS. 7 and 8. Insert 24 provides a bearing for the plug-like head 25 of an ulna screw 26 (FIG. 9). Insert 24 has a peripheral shoulder 27, with which it abuts on the underside (FIG. 6) of the ulna plate 17. Four elastically resilient hook elements 28, which form the end of a sleeve-shaped middle part 29, grip the top of the ulna plate 17, This sleeve part 29 has four slots 30 on its end, in order to form the hook elements 28. Sleeve part 29 also has an inner surface which curves in the direction of the axis 31 of insert 24 in such a manner that the cross section of the opening of insert 24 decreases in proceeding from both ends of the insert towards the center. Insert 24 is made preferably of plastics material, especially polyethylene.

The ulna screw 26 illustrated in FIG. 9 has a thread-free tip 32, a threaded section 33, a hexagonal section 34, and a cylinder-shaped screw head 25. Tip 32 is rounded on its free end and merges conically into the threaded section 33. Threaded section 33 is likewise conically shaped. The ulna screw 26 can be screwed axially into the ulna using the hex-section 34, after the head of the ulna has been removed. The cylindrical screw head 25 is journaled in insert 24 and can there be both axially displaced in the direction of axis 31 and pivoted, swiveled, about the center of the insert 24. Moreover, the ulna screw 26 can be turned about its longitudinal axis in insert 24.

FIG. 10 shows a carpal plate 35 in perspective view. Observable, in particular, are a dovetail groove 36, as well as two seats 37 and 38 and a part of a snap-lock connection 39. The seats are for receiving the heads 40 of two bone screws 41. For this purpose, the seats 37 and 38 are given a calotte shape, to match spherical sections on the screw head 40. In their remaining details, bone screws 41 are otherwise similar to the ulna screw 26. The conical shape of the thread-free screw tip provides optimal guiding of screws 41 as they are screwed into the metacarpal bones. A hexagonal Allen wrench, which cooperates with the hexagonal opening 42 in the screw head 40 of the bone screw 41, is used for screwing these screws into place.

The seats 37 and 38 have the form of a figure 8, this providing the possibility of arranging the bone screws 41 in each seat 37 and 38 in two positions. In this way, the spacing of the bone screws from one another, as well as the positions of the bone screws 41 relative to the carpal plate 35 and thus relative to the radius bone, can be optimally selected.

FIG. 12 shows that the carpal plate 35 has a wedge shape, so that the front surface with the screw exits of the seats 37 and 38 is inclined relative to the base surface bearing the dovetail groove 36. The angle of inclination is 12-degrees. It is also possible, however, to have the dovetail groove 36 on an inclined base surface, in which case the axes of the seats 37 and 38 would be orthogonal to the exit surface.

FIGS. 13 and 14 show a first embodiment of a bearing element 43, which has a dovetail tenon 47 corresponding to the dovetail groove 36 of the carpal plate 35. Moreover, the upper side 44 has an elastically resilient tongue 45, from which a lug 46 protrudes. As the bearing element 43 is connected with the carpal plate 35 using the dovetail connection 36 and 47, the lug 46 presses against the entrance incline 48 of the snap-lock connection 39. When the bearing element 43 is completely pushed into the carpal plate 35, lug 46 snaps into place in its lock position in the groove 49 of the carpal plate 35 and the bearing element 43 becomes securely locked on the carpal plate 35. The bearing element is made preferably of a plastics material, especially polyethylene.

The side lying opposite to the dovetail tenon 47 is concavely shaped and has in both the longitudinal direction (arrow 14) and in the transverse direction (arrow 15) an inwardly-directed, circular arc-shaped curvature, with the radius in the longitudinal direction being greater than the radius in the transverse direction. These concave curvatures correspond to the convex curvatures on the anchor head 9 of the anchor 5.

In addition, the bearing element 43 has a hollowed-out area 50 (FIGS. 3, 13 and 14) on a narrow side, in order to assure that the bearing element 43 does not collide with the head 25 of the ulna screw 26 during pivoting in the longitudinal direction (supination).

FIG. 15 shows a second embodiment of bearing element 43, this having an axially protruding lug 52 on its concave surface forming the second part 51 of the bearing 4. This lug 52 extends into the groove 16 (FIG. 5) of anchor head 9 and interferes with movement of bearing 4 in the longitudinal direction (arrow 14) (pronation-supination). In contrast, inclination in the transverse direction (arrow 15) remains possible afterwards as before. In this manner, the wrist prosthesis is stabilized in one direction.

In general, it is to be noted that the separate components can have different sizes, except for those elements which serve for interconnecting the components. Thus, for instance, the screws 26 and 41 can have different lengths and cross sections, the bearing element 43 can have different heights, the ulna plate 17 can be flat or curved, and its laterally protruding section 22 can protrude to different extents. Moreover, the anchor 5 can have different sizes.

A further advantage of the present invention lies in the fact that the wrist prosthesis can be used with or without ulna plate 17.

What is claimed is:

1. A wrist prosthesis, comprising:
   a first, proximal section configured to be connected to the radius bone; and
   a second, distal section configured to be connected to at least one metacarpal bone, wherein:
   each section defines a part of a curved bearing, with the part defined by said first, proximal section including a convex surface and the part defined by said second, distal section including a concave surface which engages said convex surface,
   said second, distal section includes a carpal plate in which at least one element is journaled for connection to said at least one metacarpal bone,
   said carpal plate includes a seat,
   said second, distal section further includes a screw connected to the metacarpal bone,
   said screw having a head, and
   said head is received by said seat.

2. The wrist prosthesis as defined in claim 1, wherein said first, proximal section includes an anchor which is cemented in the radius bone.

3. The wrist prosthesis as defined in claim 2, wherein said anchor includes an asymmetrically-shaped pin which extends into the radius bone, and a head extending above the radius bone.

4. The wrist prosthesis as defined in claim 3, wherein said anchor head forms part of said curved bearing.

5. The wrist prosthesis as defined in claim 3, farther comprising:
   an ulna-radius connecting means, wherein said anchor head has a side facing said pin which defines an area for receiving said ulna-radius connecting means.

6. The wrist prosthesis as defined in claim 5, wherein said ulna-radius connecting means comprises an ulna plate.

7. The wrist prosthesis as defined in claim 6, further comprising:
   an ulna screw, wherein said ulna plate extends laterally beyond said anchor head and has a seat for said ulna screw.

8. The wrist prosthesis as defined in claim 7, further comprising:
   an insert, wherein said insert is provided in said seat for said ulna screw, and wherein said ulna screw is movably connected with said ulna plate by means of said insert.

9. The wrist prosthesis as defined in claim 8, wherein at least one of: said bearing element and said insert are made of plastic.

10. The wrist prosthesis as defined in claim 9, wherein said plastic is PE.

11. The wrist prosthesis as defined in claim 8, wherein said ulna screw is journaled in said insert such that it can do one of: swivel, undergo axial displacement, and swivel and undergo axial displacement relative to said ulna plate.

12. The wrist prosthesis as defined in claim 1, wherein said second, distal section includes a screw connected to the metacarpal bone.

13. The wrist prosthesis as defined in claim 1, wherein two screws are included each with a head, said heads being received in a respective seat, and
   each seat has a longitudinal extent with at least two seating positions for a respective head.

14. The wrist prosthesis as defined in claim 13, wherein said seats have the form of a figure 8.

15. The wrist prosthesis as defined in claim 1, wherein said first, proximal section defines an axis, and
   the wrist has an inclination plane, and each seat defines an axis which is inclined in the inclination plane by an angle of between 5° to 15° relative to the axis of said first, proximal section.

16. The wrist prosthesis as defined in claim 15, wherein said angle is 12°.

17. The wrist prosthesis as defined in claim 1, further comprising:
   a bearing element, wherein said first, proximal section is connected to said carpal plate by said bearing element.

18. The wrist prosthesis as defined in claim 17, wherein said bearing element defines one part of said curved bearing.

19. The wrist prosthesis as defined in claim 17, wherein said bearing element includes a lug, wherein said first, proximal section includes an anchor including an asymmetrically-shaped pin and a head, and wherein said head has a groove for receiving said lug, so that said curved bearing is stabilized relative to the pronation-supination direction, while inclination of said curved bearing remains unaffected.

20. The wrist prosthesis as defined in claim 17, wherein said bearing element and said carpal plate are connected by a dovetail connection.

21. The wrist prosthesis as defined in claim 17, wherein said bearing element and said carpal plate are connected by a snap-lock connection.

22. The wrist prosthesis as defined in claim 17, wherein said bearing element and said carpal plate are connected by a dovetail connection and a snap-lock connection.

23. The wrist prosthesis as defined in claim 1, wherein said convex surface defines a circular arc curvature in the pronation-supination direction and in the inclination direction.

24. The wrist prosthesis as defined in claim 1, wherein said convex surface and said concave surface have a longitudinal extent and a transverse extent.

25. A wrist prosthesis, comprising:
   a first, proximal section configured to be connected to the radius bone; and
   a second, distal section configured to be connected to at least one metacarpal bone, wherein:
      each section defines a part of a curved bearing, with the part defined by said first, proximal section including a convex surface and the part defined by said second, distal section including a concave surface which engages said convex surface, and
      at least one of said first, proximal section and second, distal section are assembled from modularly combinable components which have different sizes.

* * * * *